United States Patent [19]

Reinhardt et al.

[11] Patent Number: 4,871,712
[45] Date of Patent: Oct. 3, 1989

[54] DECYLOXY-SUBSTITUTED TEREPHTHALIC ACID COMPOUNDS AND METHOD OF SYNTHESIS

[75] Inventors: Bruce A. Reinhardt, New Carlisle; Marilyn R. Unroe, Dayton, both of Ohio

[73] Assignee: The United States of America as represented by the Secretary of the Air Force, Washington, D.C.

[21] Appl. No.: 241,646

[22] Filed: Sep. 8, 1988

[51] Int. Cl.⁴ .............................................. C07C 65/00
[52] U.S. Cl. ...................................... 562/473; 560/64
[58] Field of Search ........................... 562/473; 560/64

[56] References Cited

U.S. PATENT DOCUMENTS

| | | | |
|---|---|---|---|
| 2,821,520 | 1/1958 | Burnett | 562/473 |
| 2,894,934 | 7/1959 | Burkhardt | 562/473 |
| 3,078,314 | 2/1963 | Monnikendam | 560/64 |
| 4,453,004 | 6/1984 | Nelson | 562/473 |

*Primary Examiner*—Paul J. Killos
*Attorney, Agent, or Firm*—Charles E. Bricker; Donald J. Singer

[57] ABSTRACT

Provided are dialkyloxy-substituted terephthalic acids of the formula

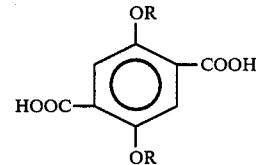

wherein R is an alkyl group having about 8 to 12 carbon atoms.

Also provided is a method for preparing these dialkyloxy-substituted terephthalic acids.

3 Claims, No Drawings

DECYLOXY-SUBSTITUTED TEREPHTHALIC ACID COMPOUNDS AND METHOD OF SYNTHESIS

RIGHTS OF THE GOVERNMENT

The invention described herein may be manufactured and used by or for the Government of the United States for all governmental purposes without the payment of any royalty.

BACKGROUND OF THE INVENTION

This invention relates to 2,5-bisalkloxyterephthalic acid and to a method for preparing these compounds.

There is a current need for acid stable, amorphous, high molecular weight polymers for use as theremoplastic matrices in molecular composites. The thermoplastics previously used generally show poor compatibility with aromatic heterocyclic rigid rod polymers due to differences in structure. These previously used theremoplastics also generally have high glass transition temperatures or melting points, thus making them difficult to consolidate into molecular composites.

The present invention provides dicarboxylic acid monomers with long alkyloxy pendant groups which, when polymerized with an appropriate bis-o-aminophenol monomer, provide polybenzoxazole polymers with glass transition temperatures below about 100° C. The structural similarity of the aromatic heterocyclic backbone of such polymers helps increase compatibility with aromatic heterocyclic rigid rod polymers.

Accordingly, it is an object of this invention to provide dicarboxylic acid monomers with long alkyloxy pendant groups.

It is another object of this invention to provide a method for preparing these monomers.

Other objects and advantages of the present invention will be apparent to those skilled in the art.

DESCRIPTION OF THE INVENTION

In accordance with the present invention, there is provided a compound of the formula

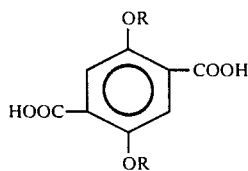

wherein R is an alkyl group having about 8 to 12 carbon atoms.

Also provided is a method for preparing these dialkyloxy-substituted terephthalic acids.

The compounds of this invention are prepared as shown by the following reactions:

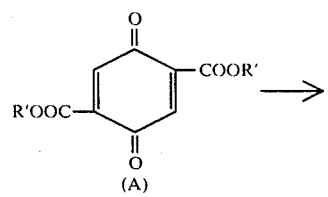
(A)

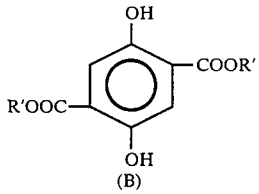
(B)

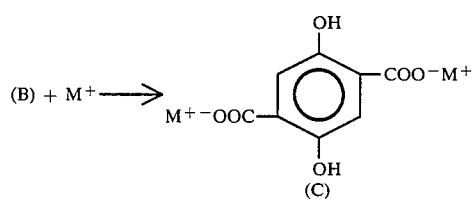
(C)

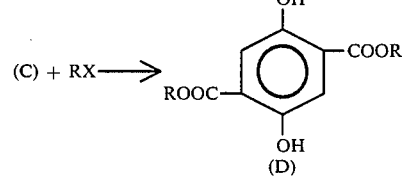
(D)

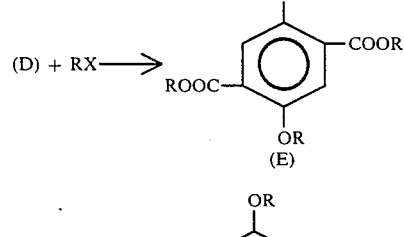
(E)

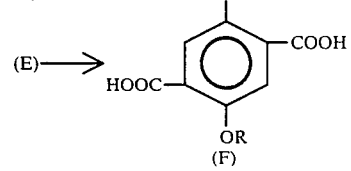
(F)

wherein R is a $C_8$ to $C_{12}$ alkyl group, and R' is a $C_1$ to $C_4$ alkyl group; wherein X is a halogen, such as Cl or Br; and wherein M is an alkali metal.

In step I, above, a dialkyl-1,4-dioxo-cyclohexane-2,5-dicarboxylate (A) is converted to the corresponding 2,5-dihydroxy dialkylterephthalate (B) using a suitable agent for aromatization of the quinone structure, such as, for example, palladium on carbon of activated manganese dioxide in a suitable solvent, such as toluene, xylene or the like. The reaction may be carried out by heating the quinone ester (A) with the aromatizing agent at a temperature of about 100° C. to 150° C. for about 4 to 24 hours.

In step II above, the substituted hydroquinone (B) is reacted with an alkali metal hydroxide, such as NaOH or KOH to form the corresponding metal salt (C). The reaction is carried out under suitable reaction conditions, such as at reflux, in a suitable solvent, such as benzene, for a time sufficient to ensure substantial conversion to the salt (C), e.g. about 1 to 24 hours.

In step III, the metal salt (C) is reacted with an alkyl halide in the presence of a phase transfer catalyst, such as tris [2-(2-methoxyethoxy)ethyl]amine to form the 2,5-dihydroxy-bisalkyl-terephthalate (D). Since it is unnecessary to recover the metal salt (C) in the preceding step, the reaction may be carried out using the same solvent. The reaction is carried out by heating the reaction mixture to about 100° C. to 150° C. for about 4 to 24 hours. At the end of the reaction period, the product (D) may be recovered by crystallization.

In step IV, the 2,5-dihydroxy-bisalkylterephthalate (D) is reacted with an alkyl halide containing 8 to 12 carbon atoms in the presence of a suitable base, such as potassium carbonate, to form the corresponding 2,5-dialkoxybisalkylterephthalate (E). The reaction is carried out in a suitable solvent, such as sulfolane, at a temperature of about 125° C. to 175° C. for about 8 to 25 hours. The reaction product may be recovered using conventional methods, such as by pouring the reaction mixture into a non-solvent for the product, such as water, and separating the product therefrom.

In step V, the 2,5-dialkyloxy-bisalkylterephthalate (E) is hydrolyzed to the corresponding 2,5-dialkyloxy terephthalic acid (F). The hydrolysis may be carried out in a suitable solvent, such as diethyl ether, with an alkali metal alkoxide using a small amount of water as a catalyst. The reaction is commenced at a low temperature, e.g., about 0°–5° C. The reaction mixture is then allowed to warm to about room temperature. The reaction is carried on for about 8 to 36 hours.

The 2,5-dialkoxy terephthalic acids of this invention are useful for preparing amorphous thermoplastic polybenzoxazoles having repeating units of the formula:

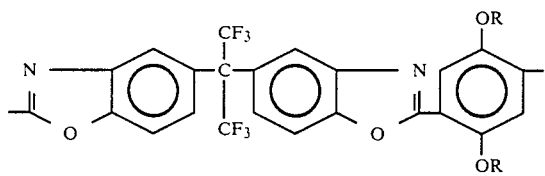

wherein R is an alkyl group having 8 to 12 carbon atoms. These polymers have a low glass transition temperature, generally below about 150° C. Preparation of these polymers is described in Reinhardt, application Ser. No. 241,646, filed of even date herewith.

The following examples illustrate the invention.

EXAMPLE I

Preparation of 2,5-Dihydroxy-dimethylterephthalate

A mixture of 100.0g (0.438 mol) of dimethyl-1,4-dioxocyclohexane-2,5-dicarboxylate and 49.53g (0.570 mol) of activated manganese dioxide in 800 ml of toluene was heated to 100° for 20 hours. The reaction mixture was then allowed to cool slightly and hot filtered. The filtrate was allowed to cool to room temperature and the resulting crystals collected on a Buchner funnel and air dried to give 20.88g (21%, mp 176° C.). A second crop was recovered from the filtrate to give an additional 4.96g (5%).

Anal. Cald'd for ($C_{10}H_{10}O_6$): C,53.09; H,4.46. Found: C,53.24; H,4.46.

Mass Spectrum (EIMS): m/z =226 (68%, M+), 194 (100%, M-CH$_3$OH).

EXAMPLE II

Preparation of 2,5-Dihydroxy-bisdecyloxyterephthalate

A mixture of 10.0g (0.043 mol) of the diester and 4.87g (0.086 mol) of 1N methanolic potassium hydroxide in 100ml of benzene was heated to reflux under N$_2$. The water formed during the course of the reaction was removed as an azeotrope with the benzene solvent by distillation to form the orange dipotassium salt. Upon cooling to 30° C., 19.21g (0.087 mol) of 1-bromodecane and 28.10g (0.087 mol) of tris[2-(2-methoxyethoxy)ethyl]amine (TMEEA) were added and the reaction mixture was heated to 110° C. for 20 hours. At the end of this period, the reaction mixture was filtered hot and the amine salt washed with benzene. The filtrate was allowed to cool and the crude product which precipitated was filtered and air dried. The product was purified by recrystallization from hexane (250 ml) to give 10.40g, (50%) of pale yellow plates, mp 84°–85° C. Evaporation of the initial benzene filtrate afforded additional material which upon recrystallization from hexane gave 2.17g (10%) mp 83°–86° C.

Anal. Calc'd for ($C_{28}H_{46}O_6$): C,70.26; H, 9.69. Found: C,69.80; H, 9.55.

Mass Spectrum (EIMS): m/z =478 (20%, M+), 180 (100,M-$C_{10}H_{21}$O-$C_{10}H_{21}$).

EXAMPLE III

Preparation of 2,5-bisdecyloxy-bisdecyloxyterephthalate

A mixture of 34.86g (0.073 mol) of 2,5-dihydroxybisdecyloxy-terephthalate, 35.00g (0.158 mol) of 1-bromodecane in 375 ml of sulfolane was purged under nitrogen for 30 minutes. After purging, potassium carbonate 21.14g (0.152 mol) was added and the temperature raised to 150° by means of an oil bath. The reaction was maintained at 150° for 19 hours at which time the reaction appeared to be complete by TLC (SiO$_2$,CH$_2$Cl$_2$). The reaction mixture was poured into 1600 ml of ice water and the resulting greasy precipitate filtered. The precipitate was washed with methylene chloride to remove trapped sulfolane. After air drying, the crude product was recrystallized from hexane (1400 ml). Residual sulfolane forms a layer on the bottom of the recrystallization flask but the hexane layer can be decanted. After separation, the hexane layer is cooled in the refrigerator to give white fluffy needles. Drying at room temperature under high vacuum gave 31.9g (58%), mp 61°–62° C. Successive crops recovered an additional 12.50g (23%) of white needles, mp 57°–59° C.

Anal. Cald'd for ($C_{48}H_{86}O_6$): C, 75.94; H, 11.42. Found: C, 76.00; H, 11.11.

Mass Spectrum (EIMS): m/z =759 (21%, M+), 43 (100%, C$_3$H$_6$+).

EXAMPLE IV

Preparation of 2,5-bisdecyloxyterephthalic acid

A suspension of 109.29g (0.973 mol) of potassium t-butoxide, and 4.90g of distilled water in 500 ml of diethyl ether was cooled to 0°–5° C. by means of an ice bath. To the cooled suspension was added 46.21g (0.061 mol) of 2,5-bisdecyloxy-bis-decyloxyterephthalate suspended in 450 ml additional diethyl ether. The reaction mixture was allowed to warm to room temperature overnight and after 20 hours, the resulting yellow slurry was filtered and rinsed with ether. The sticky off-white precipitate was dissolved in 1200 ml of water and extracted with two 200 ml portions of methylene chloride to remove any residual starting material or half product. The aqueous layer was acidified to a pH of 1 with concentrated HCl and a white precipitate was produced. The crude product was filtered, air dried overnight and recrystallized twice from toluene to give 19.76g (68%) of pure diacid, mp 136°–137° C.

Anal. Calc'd for ($C_{28}H_{46}O_6$): C, 70.25; H, 9.69. Found: C, 69.88; H, 9.47.

Mass Spectrum (EIMS): m/z =478 (8%, M+), 180 (100%, M-$C_{10}H_{21}$-$C_{10}H_{21}$-$H_2O$ Various modifications may be made without departing from the spirit of the invention or the scope of the appended claims.

We claim:

1. A dialkoxy-substituted terephthalic acid of the formula:

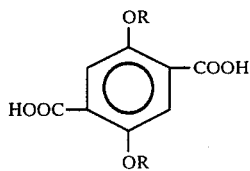

wherein R is an alkyl group having 8 to 12 carbon atoms.

2. The acid of claim 1 wherein R has 10 carbon atoms.

3. A method for preparing a dialkoxy-substituted terephthalate acid of the formula:

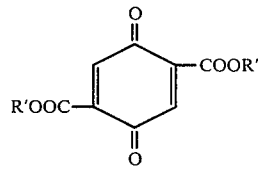

wherein R is an alkyl group having 8 to 12 carbon atoms, which comprises the steps of:

(a) treating a 2,5-dialkylcarboxylate-1,4-benzoquinone of the formula:

$$\text{R'OOC} \underset{\underset{O}{\|}}{\overset{\overset{O}{\|}}{\diagup\!\!\!\!\diagdown}} \text{COOR'}$$

wherein R' is an alkyl group having 1 to 4 carbon atoms with an aromaticizing agent to form the corresponding 2,5-dihydroxydialkylterephthalate, (b) reacting the 2,5-dihydroxydialklyterephthalate from step (a) with an alkali metal hydroxide to form the corresponding alkali metal salt:

(c) reacting the alkali metal salt of step (b) with an alkyl halide of the formula RX, wherein R is an alkyl group having 8 to 12 carbon atoms and X is Br or Cl, to form the corresponding 2,5-dihydroxydialkylterephalate;

(d) reacting the 2,5-dihydroxydialkylterephthalate from step (c) with an alkyl halide of the formula RX, as defined above, to form the corresponding 2,5-dialkoxydialkylterephthalate; and (e) hydrolyzing the 2,5-dialkoxydialkylterephthalate from step (d) to provide said dialkoxy-substitute terephthalic acid.

* * * * *